(12) United States Patent
Kanattukara et al.

(10) Patent No.: US 11,613,623 B2
(45) Date of Patent: Mar. 28, 2023

(54) CATALYTIC PYROLYSIS OF POLYSTYRENE INTO AROMATIC RICH LIQUID PRODUCT USING SPHERICAL CATALYST

(71) Applicant: INDIAN OIL CORPORATION LIMITED, Maharashtra (IN)

(72) Inventors: Bineesh Vijayan Kanattukara, Faridabad (IN); Gurmeet Singh, Faridabad (IN); Dheer Singh, Faridabad (IN); Gurpreet Singh Kapur, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 17/481,050

(22) Filed: Sep. 21, 2021

(65) Prior Publication Data
US 2022/0089831 A1    Mar. 24, 2022

(30) Foreign Application Priority Data

Sep. 21, 2020    (IN) .............................. 202021040819

(51) Int. Cl.
*C08J 11/16* (2006.01)
*B01J 8/02* (2006.01)
(Continued)

(52) U.S. Cl.
CPC ............. *C08J 11/16* (2013.01); *B01J 8/0221* (2013.01); *B01J 8/0403* (2013.01); *B01J 8/062* (2013.01);
(Continued)

(58) Field of Classification Search
None
See application file for complete search history.

(56) References Cited

U.S. PATENT DOCUMENTS 5,072,068 A    12/1991    Luo et al.
5,672,794 A     9/1997    Northemann
(Continued)

FOREIGN PATENT DOCUMENTS

WO    WO2000066656 A1    11/2000
WO    WO2005087897 A1     9/2005
(Continued)

OTHER PUBLICATIONS

Kim Young Sil et al: (1999) "Pyrolysis of polystyrene in a batch-type stirred vessel", Korean Journal of Chemical Engineering, vol. 16, No. 2, pp. 161-165, XP055891069, New York, ISSN: 0256-1115, DOI: 10.1007/BF02706830.

*Primary Examiner* — Philip Y Louie
(74) *Attorney, Agent, or Firm* — Maschoff Brennan

(57) ABSTRACT

The present invention provides a process of catalytic depolymerization of polystyrene involving a spherical catalyst, an apparatus for carrying out the depolymerization, recovering the aromatic rich liquid product and recycling the catalyst without any decrease in the catalytic performance. Further, the present invention provides that the aromatic rich liquid product includes styrene, xylene, benzene, ethyl benzene, with styrene content greater than 65%. Additionally, the catalyst involved in the depolymerization process is a spherical catalyst that is easily recovered from coke/char formed during the process and is recycled and reused without any decrease in the catalytic performance.

15 Claims, 1 Drawing Sheet

(51) Int. Cl.
*B01J 21/00* (2006.01)
*B01J 35/08* (2006.01)
*C07C 4/22* (2006.01)
*B01J 8/04* (2006.01)
*B01J 8/06* (2006.01)
*B01J 21/04* (2006.01)
*B01J 21/10* (2006.01)
*B01J 21/16* (2006.01)
*B01J 21/20* (2006.01)
*B01J 23/72* (2006.01)
*B01J 23/745* (2006.01)
*B01J 23/94* (2006.01)
*B01J 29/40* (2006.01)
*B01J 29/90* (2006.01)

(52) U.S. Cl.
CPC ............... *B01J 8/065* (2013.01); *B01J 8/067* (2013.01); *B01J 21/04* (2013.01); *B01J 21/10* (2013.01); *B01J 21/16* (2013.01); *B01J 21/20* (2013.01); *B01J 23/72* (2013.01); *B01J 23/745* (2013.01); *B01J 23/94* (2013.01); *B01J 29/40* (2013.01); *B01J 29/90* (2013.01); *B01J 35/08* (2013.01); *C07C 4/22* (2013.01); *B01J 2208/00044* (2013.01); *B01J 2208/00548* (2013.01); *B01J 2208/00752* (2013.01); *B01J 2208/00805* (2013.01); *B01J 2208/065* (2013.01); *C08J 2325/10* (2013.01); *C08J 2325/12* (2013.01)

(56) References Cited

U.S. PATENT DOCUMENTS

| | | |
|---|---|---|
| 6,380,448 B1 | 4/2002 | Sato et al. |
| 9,650,313 B2 | 5/2017 | Tippet et al. |
| 10,301,235 B1 | 5/2019 | Cavinaw et al. |
| 11,033,869 B1 * | 6/2021 | Al-Salem ............... C10B 47/24 |
| 2012/0108863 A1 * | 5/2012 | Tippet ...................... C07C 4/22 422/184.1 |

FOREIGN PATENT DOCUMENTS

| | | |
|---|---|---|
| WO | WO2005094990 A1 | 10/2005 |
| WO | 2009/145884 A1 | 12/2009 |
| WO | WO2014159260 A1 | 10/2014 |
| WO | 2018/058257 A1 | 4/2018 |
| WO | WO2019246504 A1 | 12/2019 |

* cited by examiner

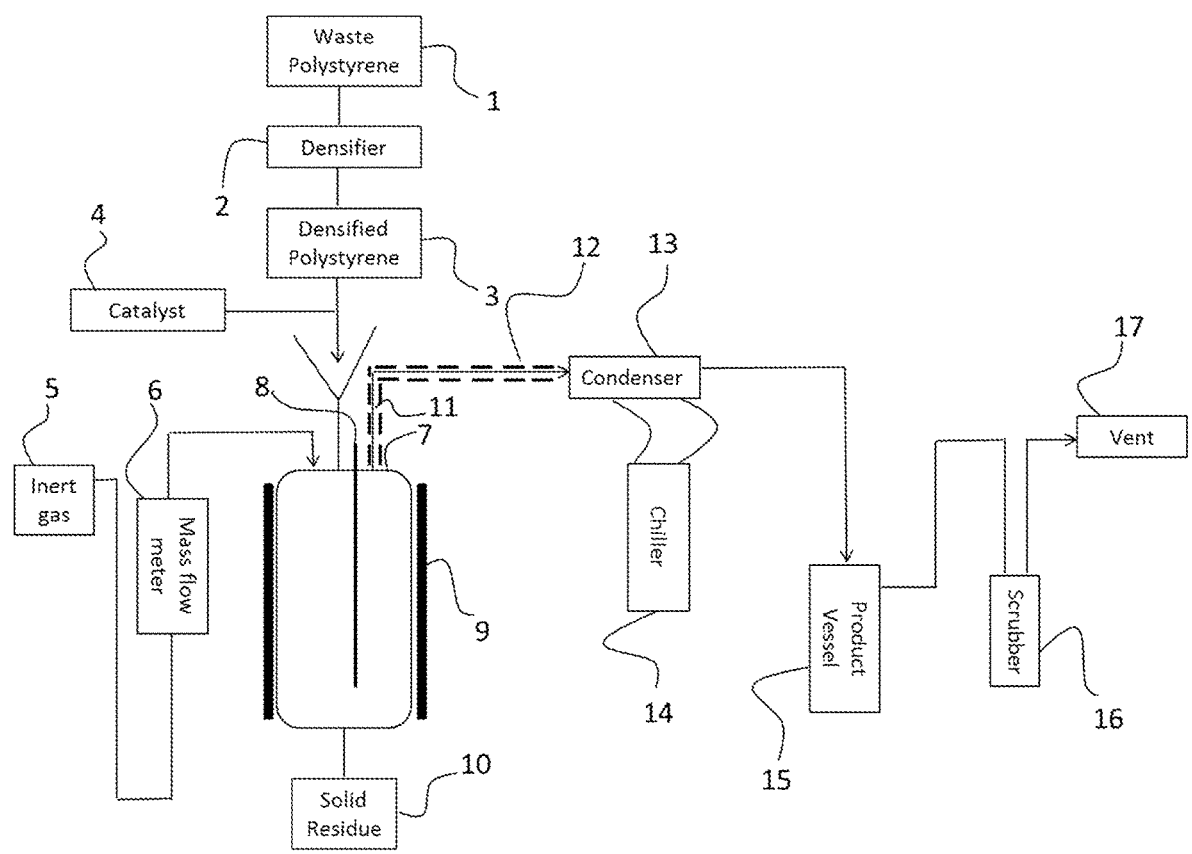

CATALYTIC PYROLYSIS OF POLYSTYRENE INTO AROMATIC RICH LIQUID PRODUCT USING SPHERICAL CATALYST

FIELD OF THE INVENTION

The present invention relates to a process of catalytic depolymerization of polystyrene involving a spherical catalyst, an apparatus for carrying out the depolymerization reaction, recovering the aromatic rich liquid product and recycling the catalyst without any decrease in the catalytic performance.

BACKGROUND OF THE INVENTION

Plastics are amongst the best innovative material that has made the life of a consumer better. However, the huge and enormous generation of waste plastics is becoming a threat to the world because plastics are non-biodegradable and remains as such for many decades. Polystyrene plastics are thermoplastic materials which are commonly used as packaging material for electrical appliances, food trays, cups, cushioning materials for fix boxes and fragile items etc. Among these, the expandable foam type polystyrene material occupies a major portion. Due to its increased volume and low density, this property makes expandable foam type polystyrene usage manifold, but this property is one of the main concerns contributing to environmental pollution. Efforts have been undertaken by many researchers to recycle the polystyrene waste plastics into useful products. Several techniques or methods have been used by researchers to recover styrene rich aromatic liquids from polystyrene waste.

Polystyrene waste not only consists of polymer being discarded after usage but also includes the polymer that is left behind after processing into desired shape and size, also including the side product or non-prime polymer.

U.S. Pat. No. 5,072,068 describes a method for recovering styrene from polystyrene scrap material through a pyrolytic reduction, which consists of loading alloy additives and metal oxide as catalyst to the pyrolyzer, with a continuous feeding of polystyrene granules of diameter 3-5 mm to the pyrolyzer at a constant rate. As the temperature of the pyrolyzer reaches 350° C., gas is introduced into the pyrolyzer. The pyrolysis was carried out in a temperature range of 450-500° C., with simultaneous feeding and distillation under reduced pressure. The yield of liquid distillate was 90% of the feed stock in weight. The recovery rate of styrene amounts to 70-75%.

U.S. Pat. No. 6,380,448 relates to a method for recovering styrene from polystyrene resin using sulfate as catalyst, most preferably metal sulfates like magnesium sulfate, sodium sulfate, iron sulfate, aluminum sulfate, calcium sulfate, potassium sulfate and antimony sulfate and the mixture of two or more sulfates. The reaction temperature was kept at 350° C. or below.

U.S. Pat. No. 5,672,794 describes a process for recovering monomeric styrene from waste plastics containing styrene polymer by thermal depolymerization, in which the waste in the form of liquid or solid is carried to a fluidized bed reactor in the presence of solid magnesium aluminum silicate as heat transfer agent, heated to a temperature of 400-700° C. and is cracked in an average residence time of 60 seconds and styrene is obtained from the gaseous cracked products.

U.S. Pat. No. 10,301,235 describes a system which includes a mixing, heating, and compacting apparatus to receive a supply of waste polystyrene and give as output, a densified polystyrene containing melt. It also describes a pyrolysis reactor where the densified polystyrene containing melt and a supply of recycled oligomers can be fed i.e pyrolyze the densified polystyrene containing melt and the recycled oligomers, to give a hydrocarbon gas stream and a solids residue stream. There is no usage of any catalyst.

U.S. Pat. No. 9,650,313 describes a process for recovering styrene monomer from a waste plastic where waste polymer is first transformed into polymer particle. These particles are then separated based on densities wherein, low density particles are completely removed from the polymer waste. The leftover polymer particles are dissolved in toluene from where undissolved polymers are removed. This polymer stream is then caustic treated, hydrotreated, and heated to a temperature below the critical temperature of the polymer stream in a preheater. The dissolved polymer particles are depolymerized to form a styrene monomer stream and the styrene monomer stream is cooled by heating the polymer stream in the preheater. The styrene monomer stream is neutralized and separated into a concentrated toluene stream including at least 50% toluene, a fuel oil stream, and a concentrated styrene stream.

WO2018058257 describes a system for continuously treating recycled polystyrene material wherein a hopper/densifier is configured to feed recycled polystyrene material. The plastic waste is turned into molten form by using an extruder and solvents like toluene or xylene. Further, the molten material can be depolymerized in a reactor using a catalyst based on catalyst such as [Fe—Cu—Mo—P]/AbO$_3$. The product can be isolated by extraction, distillation, and/or separation.

WO2009145884 describes a process to produce hydrocarbons by catalytic decomposition of plastic waste in a single step. The plastic waste is provided a thermal pretreatment to produce a liquid plastic mass, carried out in an inert gas atmosphere at a temperature varying between 110° C. and 310° C. This feed in molten state is fed into a reaction apparatus containing a bed of particles of porous inorganic material i.e the catalyst which is HZSM-5 zeolite cracking catalyst, at a temperature of 300° C. to 600° C. to generate a mixture containing hydrocarbons both in gaseous and liquid form.

The prior arts mentioned above suffer from the drawback of the disposal and recycling of the polystyrene waste into useful products, which is a major concern to the environmental pollution. Subsequently, polystyrene waste comprises one of the major portions of the municipal solid wastes. The disposal and recycling of the polystyrene waste into useful products is a major concern to the environmental pollution. To overcome such problems, depolymerization of polystyrene is required to be done. The depolymerizarion of polystyrene to styrene monomer can be done thermally or in the presence of catalysts. Previously employed catalytic systems are mainly a mixture of alloy additive and mixed oxide, various metal sulfate or mixture of two sulfate, magnesium aluminum silicate as heat transfer agent, [Fe—Cu—Mo—P]/AbO$_3$, HZSM-5 zeolite etc., for the depolymerization of polystyrene to styrene. Although, the different types of catalyst systems with different applications are known in prior art, but are with limited claims on reuse and recovery. Thus, there remains an unmet need for the development of a process of depolymerization of a polymer of styrene for removal of polystyrene waste from the environment by employing a suitable catalyst system that is easily re-activated after the depolymerization reaction.

SUMMARY OF THE INVENTION

Accordingly, the present invention provides a solution for the environmental pollution created by the polystyrene waste, by converting it into styrene rich product, which is a sustainable and circular solution for the waste plastic management. The present invention provides a process of catalytic depolymerization of polystyrene including a spherical catalyst, an apparatus for carrying out the depolymerization, recovering the aromatic rich liquid product with a liquid product yield greater than 85%. The aromatic rich liquid product includes styrene, xylene, benzene, ethyl benzene, with styrene content greater than 65%. Another feature is that the spherical catalyst is easily recovered from coke/char formed during the process and is recycled and reused without any decrease in the catalytic performance.

The present invention thus provides a process of catalytic depolymerization of polystyrene, the process comprising:
 (a) adding a polystyrene feed and a catalyst into a reactor, wherein the catalyst and the feed are added together, or the feed is added first followed by the catalyst, or the feed is added into the reactor containing the catalyst; wherein the catalyst is a spherical catalyst;
 (b) mixing of the feed with the catalyst in the reactor to obtain a mixture and heating the mixture at a rate ranging from 3 to 20° C./min in an inert atmosphere for generating vapor;
 (c) passing the vapor from the reactor to a condenser to obtain a condensate, wherein a heating tape is connected to a temperature controller in the reactor to prevent condensation of the vapor before entering the condenser; and
 (d) routing the condensate from the condenser to a liquid product collection flask and passing un-condensable gases from the condenser through a scrubber; wherein the liquid product is present in an amount ranging from 85 to 90% by weight comprising styrene in an amount ranging from 65 to 71% by weight of the liquid product.

Further, the present invention provides an apparatus for depolymerization of polystyrene, comprising:
 (a) a stainless steel cylindrical or tubular reactor (7) equipped with mass flow meter to control the flow of inert gas;
 (b) a split type single zone electrical furnace (9) with a programmable digital temperature controller for heating the reactor using an electrical or a thermal fluid system;
 (c) a K-type thermocouple (8) connected to the temperature controller to measure temperature of the reactor;
 (d) an opening provided at the top of the reactor for routing vapors generated in the reactor during depolymerization into a condenser (13);
 (e) a heating tape (12) connected to the temperature controller to prevent condensation of the vapors before entering the condenser;
 (f) a chiller (14) connected to the condenser for maintaining the temperature of the condenser;
 (g) a liquid product collection flask (15) for collecting condensate from the condenser; and
 (h) a scrubber (16) for passing un-condensable gases from the condenser.

Objectives of the Invention

It is a primary objective of the present invention to provide a process of catalytic depolymerization of polystyrene using a spherical catalyst.

It is a further objective of the present invention to provide an apparatus for carrying out the depolymerization.

Another objective of the present invention is to recover the aromatic rich liquid product and recycle the catalyst without any decrease in the catalytic performance.

BRIEF DESCRIPTION OF DRAWINGS OF THE PRESENT INVENTION

FIGURE illustrates the apparatus for depolymerization disclosed in the present invention.

DETAILED DESCRIPTION OF THE INVENTION

For the purpose of promoting an understanding of the principles of the present disclosure, reference will now be made to the specific embodiments of the present invention further illustrated in specific language to describe the same. The foregoing general description and the following detailed description are explanatory of the present disclosure and are not intended to be restrictive thereof. It will nevertheless be understood that no limitation of the scope of the present disclosure is thereby intended, such alterations and further modifications in the illustrated composition, and such further applications of the principles of the present disclosure as illustrated herein being contemplated as would normally occur to one skilled in the art to which the present disclosure relates. Unless otherwise defined, all technical and scientific terms used herein have the same meaning as commonly understood by one ordinarily skilled in the art to which this present disclosure belongs. The products, methods, and examples provided herein are illustrative only and not intended to be limiting.

The present invention covers a process of catalytic depolymerization of polystyrene including a spherical catalyst, an apparatus for carrying out the depolymerization, recovering aromatic rich liquid product and recycling the catalyst without any decrease in its catalytic performance. The present invention thus provides a process of catalytic depolymerization of polystyrene, the process comprising:
 (a) adding a polystyrene feed and a catalyst into a reactor, wherein the catalyst and the feed are added together, or the feed is added first followed by the catalyst, or the feed is added into the reactor containing the catalyst; wherein the catalyst is a spherical catalyst;
 (b) mixing of the feed with the catalyst in the reactor to obtain a mixture and heating the mixture at a rate ranging from 3 to 20° C./min in an inert atmosphere for generating vapor;
 (c) passing the vapor from the reactor to a condenser to obtain a condensate, wherein a heating tape is connected to a temperature controller in the reactor to prevent condensation of the vapor before entering the condenser; and
 (d) routing the condensate from the condenser to a liquid product collection flask and passing un-condensable gases from the condenser through a scrubber;
 wherein the liquid product is present in an amount ranging from 85% to 90% by weight comprising styrene in an amount ranging from 65% to 71% by weight of the liquid product.

In an embodiment, the raw material or feed for the process of catalyst depolymerization consists of, and not limited to, a styrene rich polymer waste. A styrene rich polymer waste must have 20% to 100% by weight styrene. In another embodiment, styrene rich polymer includes, but is not limited to, acrylonitrile butadiene styrene (ABS), styrene-butadiene (SBR) rubber, styrene-butadiene latex, styreneisoprene-styrene (SIS), styrene-ethylene/butylenes-styrene (S-EB-S), styrenedivinylbenzene (S-DVB), styrene-acrylonitrile resin (SAN), unsaturated polyesters etc.

In the detailed embodiment, the raw material or the feed is either compressed, shredded, or densified before addition to the reactor.

The catalytic depolymerization of styrene rich polymer waste is carried out using a catalyst. There are several advantages of using a catalyst for carrying out such a process. First is the temperature i.e. the volatility of the waste/feed can be achieved at relatively lower temperatures. This control is very effective as here the temperatures that are being used for depolymerization without catalyst are above 500° C. which means that the same can be achieved through usage of catalyst at much lower temperatures making the process more viable. Also, the catalytic depolymerization of the polymers proceeds faster at same temperatures as compared to thermal decomposition as they have lower activation energy. One added advantage is the superior quality of product obtained through catalytic depolymerization. In a preferred embodiment, the heating in step (b) for depolymerization of the feed is carried out at a temperature ranging from 350° C. to 500° C.

A person skilled in the art will be aware of the catalysts being used for building the monomer units i.e. polymerization. Surprisingly, the catalyst being used is for depolymerization i.e. breaking down the polymeric units.

In a detailed embodiment, the catalyst is spherical in nature and is selected from group consisting of oxides of silicon, aluminum, alumina-silica, zinc, magnesium, barium, osmium, manganese, iron, titanium or mixtures thereof. In a preferred embodiment, the catalyst is spherical, and alumina based. In another embodiment, the spherical catalyst is used at least twice before reactivation.

In a detailed embodiment, the morphology of the catalyst is spherical. A person skilled in present art will acknowledge that depolymerization of polymer produces coke and using catalytic depolymerization process, this coke/char gets deposited on the catalyst rendering it unusable for second time. There are processes to reactivate it but that requires a separate unit. The inventors surprisingly found that using spherical catalyst for depolymerization solves this problem. The catalyst recovered after separation of the feed is reactivated in the reactor itself. In an embodiment, the present invention provides that coke produced during depolymerization is removed from the catalyst and the catalyst is reactivated in the reactor without decrease in catalytic performance.

In a detailed embodiment, the used spherical catalyst is reactivated in the reactor itself. In another embodiment, the efficacy of the reactivated catalyst for de-polymerization is same i.e. it does not affect the product profile as well as the yield. In another embodiment, the separation of coke/char from the catalyst is effortless owing to the spherical morphology of the catalyst. In another embodiment, the coke/char separated is of economical value. In case of powdered catalyst, the catalyst retains part of the coke and separation of both is difficult. This has negative impact on the economic value. For the actual experiments conducted in the horizontal reactor, recovery in case of spherical catalyst has been above 90% while for cylindrical and trilobe type extrudates the recovery has been less than 75%. In the present invention, due to unique combination of chemistry and shape it was found that the catalytic performance remains the same even after the recovery The process of depolymerization is carried out in a reactor. In an embodiment, the reactor is selected from, but not limited to, fixed-bed reactor, stirred-tank reactor, microwave reactor, fluidized-bed reactor, conical spouted bed reactor (CSBR), rotary kiln reactor, screw extruder (Auger) reactor etc. The reactor is preferably, cylindrical, or tubular. The addition of feed and the catalyst is done simultaneously into the reactor or feed is added first or the feed is added into the reactor which already contains the catalyst or the catalyst is introduced after the feed has been added into the reactor. In another embodiment, the spherical catalyst is supported/bound on a substrate inside the reactor and feed is introduced over this substrate.

It is very critical that the method adopted for feed and catalyst addition, support the effective mixing of the catalyst in the feed in the reactor. In an embodiment, the weight ratio of feed to catalyst ranges from 0.1 wt % to 10 wt %, preferably, 0.5 wt % to 5 wt %.

Further, the present invention provides an apparatus for depolymerization of polystyrene, comprising:

(a) a stainless steel cylindrical or tubular reactor (7) equipped with mass flow meter to control the flow of inert gas;

(b) a split type single zone electrical furnace (9) with a programmable digital temperature controller for heating the reactor using an electrical or a thermal fluid system;

(c) a K-type thermocouple (8) connected to the temperature controller to measure temperature of the reactor;

(d) an opening provided at the top of the reactor for routing vapors generated in the reactor during depolymerization into a condenser (13);

(e) a heating tape (12) connected to the temperature controller to prevent condensation of the vapors before entering the condenser;

(f) a chiller (14) connected to the condenser for maintaining the temperature of the condenser;

(g) a liquid product collection flask (15) for collecting condensate from the condenser; and (h) a scrubber (16) for passing un-condensable gases from the condenser.

In a detailed embodiment, the apparatus for depolymerization is described in FIGURE. The reactor 7 is a stainless steel cylindrical/tubular reactor and it was loaded with waste polymer feed 3 mixed with catalyst 4 in the desired ratio having bolts, nuts and teflon seal. It is equipped with mass flow meter 6 to control the flow of inert gas 5. The reactor 7 is heated using electrical or thermal fluid system. Here the reactor 7 is heated by a split type single zone electrical furnace 9 with a programmable digital temperature controller. The temperature of the reactor 7 is measured with the help of a K-type thermocouple 8 which is connected to the temperature controller. During the depolymerization occurring at desired temperatures, the generated vapors leave out of the reactor through an opening provided at the top of the reactor. The vapors are then allowed to pass through a bent stainless-steel tube 11 which is connected to a condenser 13. A heating tape 12 connected to a temperature controller is provided on the bent stainless-steel tube 11 to prevent the condensation of the vapors before entering the condenser 13. The temperature of the condenser 13 is maintained by connecting it to a chiller 14. The condenser 13 is then connected to the liquid product collection flask 15. The non-condensable gases are allowed to pass through a scrubber 16 and finally vent off 17.

In a detailed embodiment, an inert atmosphere is maintained during depolymerization. In a preferred embodiment, the inert gas used is nitrogen or argon.

In yet another embodiment, the feed is dissolved in organic solvents such as toluene, xylenes, cymenes, or terpinenes, before performing depolymerization within the reactor. In such cases, after depolymerization step, solvent is recycled.

In an embodiment, no organic solvent is used prior to depolymerization.

In yet another embodiment, the reactor contains spacer tube, static mixer and/or annular insert. In another embodiment, the static mixer and/or annular insert is removable. As person skilled in the art will appreciate, the actual reactor temperature depends on a number of factors including size and reactor configuration. In an embodiment, the temperature of depolymerization is in a range of 250° C. to 1000° C.

In another embodiment, the depolymerization temperature is such that the feed is in molten form. The temperature of the molten feed is controlled using temperature sensors. This allows precise control of the chemical reaction catalyzed by the spherical catalyst and thus helps in aiding the temperature of depolymerization.

In an embodiment, the temperature of depolymerization is raised gradually following a rate profile. The heating profile is adjusted to avoid slow heating, as slower heating results in more random scission and a higher number of biphenyls. In another embodiment, the conversion rate of the depolymerization process using spherical catalyst is between 50 and 100%.

In a detailed embodiment, the feed is first added into the reactor and heated to the desired temperature of depolymerization followed by addition of spherical catalyst. In another embodiment, the product resulted in styrene content greater than 65% by weight.

The product generated by the depolymerization of feed is analyzed/monitored. The analysis is performed online, offline, or through combination of both online and offline. The analytical techniques utilized are known by those of skill in the art. The technique includes, but is not limited to, spectroscopy and/or chromatography, and combinations thereof. The product collected after depolymerization of feed is named as gas, liquid and solid. The yield of liquid was calculated by the ratio of mass of liquid product collected to the initial mass of the reactant fed. The solid yield (coke+in volatile product) was calculated by the ratio of solid products produced after the reaction to the initial reactant fed. Gas yield was calculated from the difference between 100 and the total yield of liquid and solid product.

In a further embodiment, the liquid product is greater than 85% by weight. In another embodiment, the liquid is aromatic rich product. In another embodiment, the aromatic product includes styrene, xylene, benzene, ethyl benzene, with styrene content greater than 65% by weight.

Technical Advantages of the Invention

The present invention has the following advantages:
Using a spherical catalyst for depolymerization of the polystyrene to styrene rich aromatic liquid product
Easy recovery of the catalyst from coke/char formed during the process
Catalyst can be recycled and reused without any decrease in the catalytic performance

EXAMPLES

The following examples are included herein for illustrative purposes only. Those skilled in the art will appreciate that many modifications may be made in the invention without changing the essence of invention.

Example 1

The raw material or feed was weighed and introduced into the reactor. The alumina-based spherical catalyst was weighed (~1 wt %) and introduced into the vertical reactor along with the feed. It was ensured that nitrogen flow was continuously passed to maintain inert atmosphere and the reactor was sealed. The reactor was heated by a split type single zone electrical furnace with a programmable digital temperature controller to 460° C. The temperature of the reactor was measured with the help of a K-type thermocouple which is connected to the temperature controller. The heating rate was 20° C./min. As the temperature within the reactor is achieved, the generated vapours escape out of the reactor through an opening provided at the top of the reactor. The vapours are then allowed to pass through a bent stainless-steel tube which is connected to a condenser. A heating tape connected to a temperature controller was provided on the bent stainless-steel tube to prevent the condensation of the vapors before entering the condenser. The temperature of the condenser was maintained by connecting it to a chiller. The condenser was then connected to the liquid product collection flask. The un-condensable gases were then allowed to pass through a scrubber and finally vented to a hood. The product consisted of solid, liquid and gas. The liquid product was 86% by weight containing 66% styrene by weight.

Example 2

The same procedure was followed as described in Example 1 but here the catalyst was in powder form. The product consisted of solid, liquid and gas. The liquid product was 85% by weight containing 65% styrene by weight. However, in this case the catalyst remained part of the coke and the separation was not possible.

Example 3

The same procedure was followed as described in Example 1 but here the catalyst was FCC catalyst. The product consisted of solid, liquid and gas. The liquid product was 80% by weight containing 65% styrene by weight.

Example 4

The same procedure was followed as described in Example 1 but here the catalyst was ZSM-5 catalyst. The product consisted of solid, liquid and gas. The liquid product was 80% by weight containing 59% styrene by weight.

Example 5

The same procedure was followed as described in Example 1 but here the catalyst was halloysite clay. The product consisted of solid, liquid and gas. The liquid product was 80% by weight containing 60% styrene by weight.

Example 6

The same procedure was followed as described in Example 1 but here the catalyst was MgO. The product consisted of solid, liquid and gas. The liquid product was 82% by weight containing 62% styrene by weight.

Example 7

The same procedure was followed as described in Example 1 but here the catalyst was CaO. The product consisted of solid, liquid and gas. The liquid product was 83% by weight containing 61% styrene by weight.

Example 8

The same procedure was followed as described in Example 1 but here the catalyst was CuO. The product consisted of solid, liquid and gas. The liquid product was 82% by weight containing 71% styrene by weight.

Example 9

The same procedure was followed as described in Example 1 but here the catalyst was $Fe_2O_3$. The product consisted of solid, liquid and gas. The liquid product was 79% by weight containing 63% styrene by weight.

Example 10

The same procedure was followed as described in Example 1 but here the catalyst was recycled spherical alumina catalyst. The product consisted of solid, liquid and gas. The liquid product was greater than 85% by weight containing greater than 65% styrene by weight.

Example 11

The same procedure was followed as described in Example 1 but here the polystyrene feed was dissolved in the styrene rich aromatic pyrolysis oil in a 1:1 weight ratio. The obtained liquid product was 75% by weight containing 62% styrene by weight.

Example 12

The experiment was conducted as per Example 1 in a horizontal type reactor. The recovery of spherical catalyst was 90% after the reaction. The obtained liquid product was 90% by weight containing 71% styrene by weight.

Example 13

The experiment was conducted as per Example 12 using cylindrical catalyst. The recovery of cylindrical catalyst was 80% after the reaction. The obtained liquid product was 87% by weight containing 69% styrene by weight.

Example 14

The experiment was conducted as per Example 12 using trilobe catalyst. The recovery of trilobe catalyst was 73% after the reaction. The obtained liquid product was 85% by weight containing 65% styrene by weight.

The invention claimed is:

1. A process of catalytic depolymerization of polystyrene, the process comprising:
   (a) adding a polystyrene feed and a catalyst into a reactor, wherein the catalyst and the feed are added together, or the feed is added first followed by the catalyst, or the feed is added into the reactor containing the catalyst; wherein the catalyst is a spherical catalyst;
   (b) mixing the feed with the catalyst in the reactor to obtain a mixture and heating the mixture at a rate ranging from 3 to 20° C./min in an inert atmosphere for generating a vapor;
   (c) passing the vapor from the reactor to a condenser to obtain a condensate, wherein a heating tape is connected to a temperature controller to prevent condensation of the vapor before entering the condenser; and
   (d) routing the condensate from the condenser to a liquid product collection flask to collect a liquid product, and passing non-condensable gases from the condenser through a scrubber;
      wherein the liquid product is present in an amount ranging from 85% to 90% by weight of a total weight of a solid, a liquid and a gas exiting the reactor, and wherein the liquid product comprises styrene in an amount ranging from 65% to 71% by weight of the liquid product.

2. The process as claimed in claim 1, wherein the feed is a styrene rich polymer waste comprising styrene in an amount ranging from 20% to 100% by weight, wherein the styrene rich polymer is selected from the group consisting of acrylonitrile butadiene styrene (ABS), styrene-butadiene (SBS) rubber, styrene-butadiene latex, styrene-isoprene-styrene (SIS), styrene-ethylene/butylenes-styrene (S-EB-S), styrenedivinylbenzene (S-DVB), styrene-acrylonitrile resin (SAN), unsaturated polyesters, and mixtures thereof.

3. The process as claimed in claim 1, wherein the feed is compressed, shredded, or densified before addition to the reactor.

4. The process as claimed in claim 1, wherein the heating in step (b) for depolymerization of the feed is carried out at a temperature ranging from 350° C. to 500° C.

5. The process as claimed in claim 1, wherein the spherical catalyst is selected from the group consisting of alumina-silica and oxides of silicon, aluminum, zinc, magnesium, barium, osmium, manganese, iron, titanium, and mixtures thereof.

6. The process as claimed in claim 5, wherein the spherical catalyst is supported on a substrate inside the reactor and the feed is introduced over the substrate.

7. The process as claimed in claim 1, wherein coke produced during depolymerization is removed from the spherical catalyst and the spherical catalyst is reactivated in the reactor without decrease in catalytic performance.

8. The process as claimed in claim 1, wherein the reactor is cylindrical or tubular and is selected from a fixed-bed reactor, a stirred-tank reactor, a microwave reactor, a fluidized-bed reactor, a conical spouted bed reactor (CSBR), a rotary kiln reactor, and a screw extruder (Auger) reactor.

9. The process as claimed in claim 1, wherein mixing the feed with the catalyst comprises mixing 0.1 to 10 wt % of the catalyst based on a weight of the feed.

10. The process as claimed in claim 1, wherein, the feed is dissolved in an organic solvent selected from the group consisting of toluene, xylenes, cymenes, and terpinenes, wherein the solvent is recycled after depolymerization.

11. The process as claimed in claim 1, wherein conversion rate of the process using the spherical catalyst ranges between 50 and 100%.

12. An apparatus for depolymerization of polystyrene, the apparatus comprising:
    (a) a stainless steel cylindrical or tubular reactor equipped with a mass flow meter to control the flow of an inert gas, wherein the stainless steel cylindrical or tubular reactor is configured to polystyrene feed and a spherical catalyst;

(b) a split type single zone electrical furnace with a programmable digital temperature controller for heating the reactor using an electrical or a thermal fluid system, wherein the reactor is heated at a rate ranging from 3 to 20° C./min;

(c) a K-type thermocouple connected to the programmable digital temperature controller to measure a temperature of the reactor;

(d) an opening provided at a top of the reactor for routing vapors generated in the reactor during depolymerization of the polystyrene feed into a condenser;

(e) a heating tape connected to the programmable digital temperature controller to prevent condensation of the vapors before entering the condenser;

(f) a chiller connected to the condenser for maintaining a temperature of the condenser;

(g) a liquid product collection flask for collecting a condensate from the condenser, wherein the condensate is a liquid product and is present in an amount ranging from 85% to 90% by weight of a total weight of a solid, a liquid and a gas exiting the reactor, and wherein the liquid product comprises styrene in an amount ranging from 65% to 71% by weight of the liquid product; and (h) a scrubber for passing un-condensable gases from the condenser.

13. The apparatus as claimed in claim 12, wherein the reactor is a fixed-bed reactor, a stirred-tank reactor, a microwave reactor, a fluidized-bed reactor, a conical spouted bed reactor (CSBR), a rotary kiln reactor, or a screw extruder (Auger) reactor.

14. The apparatus as claimed in claim 12, wherein the reactor comprises a spacer tube, a static mixer, or an annular insert.

15. The apparatus as claimed in claim 14, wherein the static mixer, or the annular insert is removable.

* * * * *